United States Patent [19]
Zurbrügg

[11] Patent Number: 5,522,394
[45] Date of Patent: Jun. 4, 1996

[54] IMPLANTABLE MEASURING PROBE FOR MEASURING THE FLOW VELOCITY OF BLOOD IN HUMANS AND ANIMALS

[76] Inventor: Heinz R. Zurbrügg, Bündackerstrasse 158, CH-3047 Bremgarten, Switzerland

[21] Appl. No.: 258,938

[22] Filed: Jun. 13, 1994

[30] Foreign Application Priority Data

Jun. 15, 1993 [DE] Germany ............... 43 19 812.0

[51] Int. Cl.⁶ ................................................ A61B 8/12
[52] U.S. Cl. ................................................ 128/662.06
[58] Field of Search ................ 128/662.03–662.04, 128/662.06

[56] References Cited

U.S. PATENT DOCUMENTS

| | | | |
|---|---|---|---|
| 3,568,661 | 3/1971 | Franklin | 128/661.08 |
| 4,459,854 | 7/1984 | Richardson et al. | 128/662.03 X |
| 4,947,854 | 8/1990 | Rabinovitz et al. | 128/662.04 |
| 5,205,292 | 4/1993 | Czar et al. | 128/662.03 |
| 5,271,406 | 12/1993 | Ganguly et al. | 128/662.06 |
| 5,291,896 | 3/1994 | Fonger et al. | 128/662.06 X |

FOREIGN PATENT DOCUMENTS

| | | |
|---|---|---|
| 1574194 | 7/1969 | France. |
| 1439592 | 6/1976 | United Kingdom. |
| WO91/16000 | 10/1991 | WIPO. |

OTHER PUBLICATIONS

Proceedings of the Annual International Conference of the IEEE Engineering in Medicine and Biology Society, vol. 11, No. 4/6, Nov. 9, 1989, Seattle, pp. 1106–1107, "Implantable doppler ultrasonic vessel patency monitor." "A Removable Extraluminal Doppler Probe for Continuous Monitoring of Changes in Cardiac Output," Doppler Monitoring of Cardiac Output—vol. 2, Aug., 1983, pp. 357–362.

"Doppler Ultrasound in the Diagnosis of Vascular Occlusion in Renal Transplantation," Transplantation, vol. 33, No. 5, 1982, pp. 547–551.

*Primary Examiner*—Francis Jaworski
*Attorney, Agent, or Firm*—Staas & Halsey

[57] ABSTRACT

An implantable measuring probe, preferably an ultrasonic probe, for measuring the flow velocity of blood in natural blood vessels or replacement blood vessels of humans and animals. The measuring probe is provided with a rod-shaped probe head arranged at the end of a probe cable and in which a sensor, preferably a piezoelectric crystal, is inserted, and with a device for holding the probe head on the blood vessel. The irradiating and receiving surface of the sensor has an elongate shape, its longitudinal extension being at least as large as the inner diameter of the blood vessel in which the measurement is to be carried out. This surface extends with its longitudinal extension substantially parallel to the longitudinal axis of the rod-shaped probe head. Furthermore, this surface is orientated in such a manner to the holding device that it extends in the case of the probe head secured to the vessel with its longitudinal extension approximately perpendicular to the blood flow direction in the vessel.

25 Claims, 4 Drawing Sheets

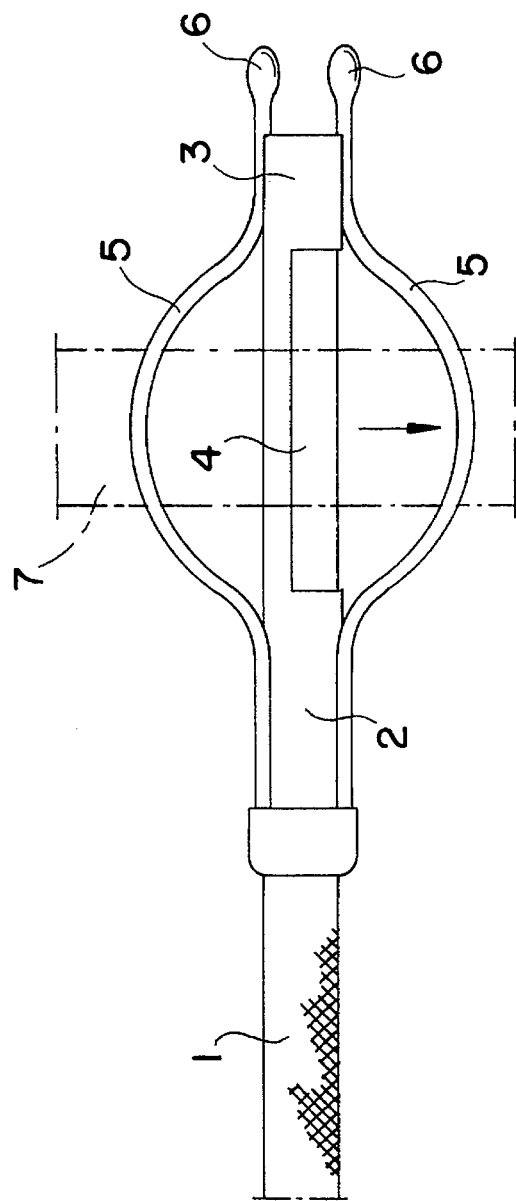
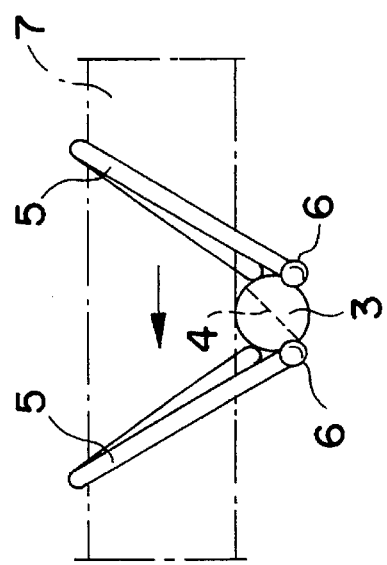

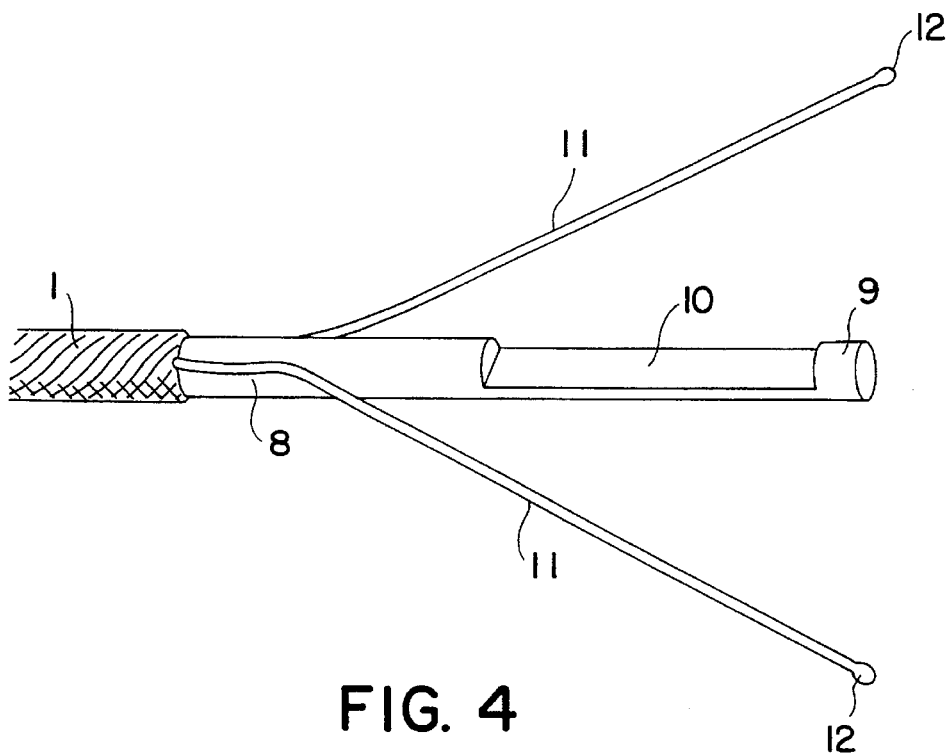
FIG. 4
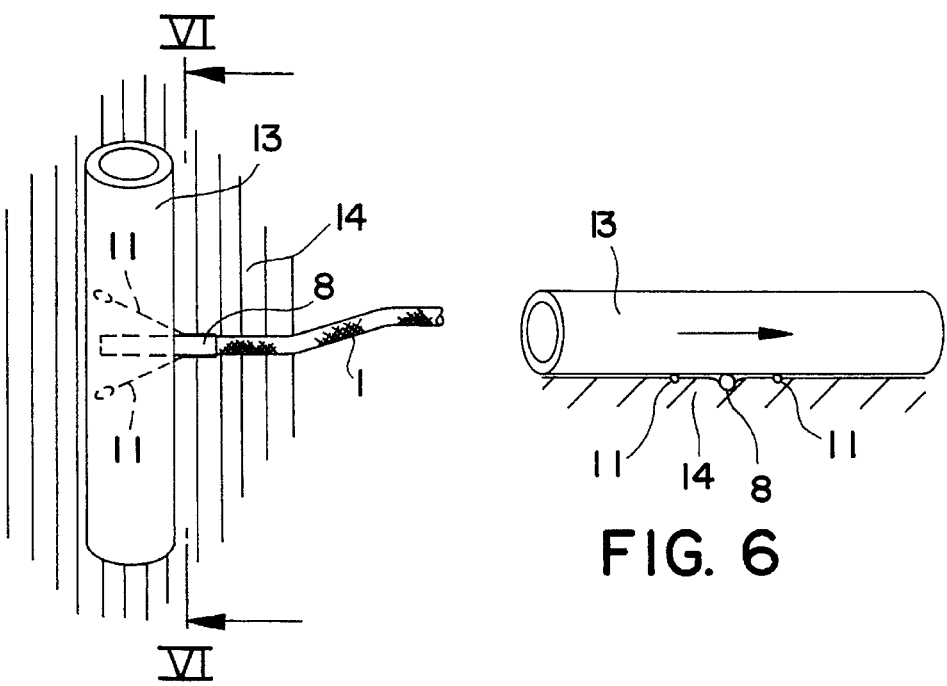
FIG. 5
FIG. 6

IMPLANTABLE MEASURING PROBE FOR MEASURING THE FLOW VELOCITY OF BLOOD IN HUMANS AND ANIMALS

BACKGROUND OF THE INVENTION

1. Field of the Invention

The present invention relates to an implantable measuring probe, and more particularly, to an ultrasonic probe for measuring the flow velocity of blood in natural blood vessels or replacement blood vessels of humans and animals.

2. Description of the Related Art

Implantable ultrasonic probes of the type mentioned above are already known for measuring the flow velocity of blood and have a piezoelectric crystal of approximately circular or quadratic shape (U.S. Pat. No. 4,947,854). As the irradiating and receiving surface of the piezoelectric crystal in the known ultrasonic probes is relatively small in comparison to the inner cross-section of the blood vessel and it cannot always be ensured in operations that this surface on the probe head is positioned with respect to the blood vessel in such a manner that that cross-section of the blood vessel essential for the measurement is irradiated with certainty, considerable measuring errors can occur with the known ultrasonic probes. This is particularly the case when the maximum flow velocities in the center of the blood vessel are not detected with the ultrasonic probe. This danger is of considerable significance in practice. Signal optimization problems in the implantation of the conventional ultrasonic probes can lead the surgeon to fix the probe too strongly to the vessel or its surroundings, which increases the danger of injuries and/or secondary bending of the blood vessels. Additionally, these measures are of often connected with relevant time losses during the operation.

SUMMARY OF THE INVENTION

It is therefore the object of the invention to provide an implantable measuring probe of the type initially mentioned, in which the beams transmitted by the sensor form such a fan what an optimal measuring result is guaranteed even in the case of normally unavoidable inaccuracies in securing the probe to the blood vessel. This object is solved by the design of the measuring probe according to the present invention. On account of the elongate form and the size of the longitudinal extension of the irradiating and receiving surface of the sensor and its arrangement on the blood vessel, which is achieved by the holding device, an optimal measuring result will be achieved even in the case of unavoidable deviations in the orientation of the irradiating and receiving surface from the ideal position.

In a preferred embodiment of the inventive probe, the longitudinal extension of the irradiating and receiving surface of its sensor is at least as large as 1½ times the inner diameter of the blood vessel in which the measurement is to be taken. Usefully, the irradiating and receiving surface of the sensor extends essentially over a large portion and at least half of the longitudinal extension and substantially across the entire cross-sectional width of the rod-shaped probe head.

Advantageously, the holding device consists of at least one clasp mounted to the probe head and by means of which the probe head can be placed onto the blood vessel. The clasp can be formed by the probe head and at least one band or wire piece which is secured with its one end approximately at or in the vicinity of the rear end of the probe head connected with the probe cable and extends at one side of the probe head substantially in its longitudinal direction. The band or wire piece is usefully elastically flexible such that the probe head positioned on a blood vessel can be pulled off the blood vessel by pulling the probe cable in the longitudinal direction of the head and can be removed without surgery from the body of the patient. In this case, the band or wire pieces can bend onto the probe head or lie against it.

The invention also relates to the manner of measuring the flow velocity (of the blood flow) in blood vessels of humans and animals with the aid of an ultrasonic probe, the probe head of which arranged at the end of a probe cable has an elongate irradiating and receiving surface which according to the invention is characterized in that the probe head is arranged in such a manner on the blood vessel that the irradiating and receiving surface extends with its longitudinal extension approximately perpendicularly to the blood flow direction in the blood vessel and with its transverse extension at an angle of 0° to 90° to the blood flow direction.

BRIEF DESCRIPTION OF THE DRAWINGS

Two particularly useful embodiments of the inventive ultrasonic probe described in more detail in the following are shown in the drawings, in which:

FIG. 2 shows the probe head according to FIG. 1 in plan view;

FIG. 3 shows the probe view according to FIG. 1 in front view;

FIG. 4 shows the probe head of the second exemplified embodiment in slanted view;

FIG. 5 shows the probe head of the second exemplified embodiment in plan view, secured between a blood vessel and the surrounding supporting tissue;

FIG. 6 shows a section through the probe head according to FIGS. 4 and 5 and its securing along line VI—VI in FIG. 5.

DETAILED DESCRIPTION OF THE PREFERRED EMBODIMENTS

Figure 1:
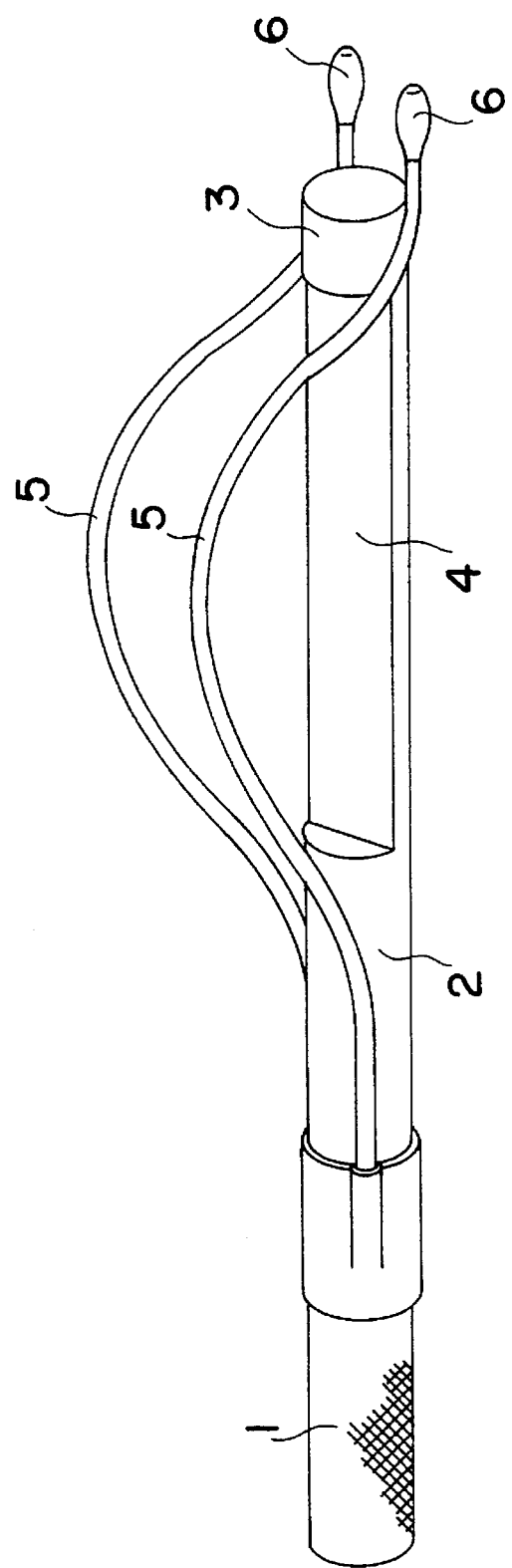
FIG. 1 shows the probe of the first exemplified embodiment in slanted view.

Referring to FIG. 1, the probe cable is shown with reference sign 1 by means of which the probe is coupled to the ultrasonic device, not shown in the drawing, and in which the data gathering and evaluation of the measurement is carried out. At the forward end of the probe cable is the probe head 2, which is rod-shaped with a substantially circular cross-section and is usefully made of stainless steel. In the probe head in the vicinity of the forward end face 3 thereof, there is a piezoelectric crystal which has an elongate, planar or slightly curved irradiating and receiving surface 4 which is set back from the circular peripheral cross section of the probe head.

Fastening wires 5 are secured at the rear end of the probe head 2 connected with the probe cable 1 and on two opposite sides of the head to which the irradiating and receiving surface 4 of the piezoelectric crystal extends at an angle of approximately 45° and serve to fasten the probe head to the blood vessel in which the measurement is to be carried out. The fastening wires are usefully of stainless spring steel.

Beginning from its rearward end, they initially extend beside the probe head parallel to its longitudinal extension to then bend away from the probe head and each other in the region of the irradiating and receiving surface 4, their mutual spacing increasing substantially (see FIG. 2 and 3). The fastening wires 5 are then bent again with their forward ends to near the forward end 3 of the probe head 2, in which position they project with these ends somewhat beyond the forward end face of the probe head. The fastening wires 5 have enlargements 6 at their ends in order to prevent excessive damage to tissue when implanting the probe head.

FIG. 2 and 3 show that on account of the arrangement and shape of the fastening wires 5, the probe head can be placed in such a manner on the blood vessel 7 in which the measurement is to be taken and aligned with respect to this in such a manner that the irradiating and receiving surface 4 extends with its longitudinal extension substantially perpendicularly to the blood flow direction in blood vessel 7 and with its transverse extension at an angle of approximately 45° to the blood flow direction (FIG. 2 and 3).

The attachment of the probe head 2 with its fastening wires 5 to the blood vessel 7 ensues in that the fastening wires 5 are bent with their forward ends away from the forward end of the probe head and the probe head is simultaneously pushed in the direction of its longitudinal extension onto the blood vessel 7, the enlargements 6 preventing damage to the tissue.

In the exemplified embodiment shown in FIG. 1 to 3, the longitudinal extension of the irradiating and receiving surface 4 of the piezoelectric crystal is approximately twice as large as the inner diameter of the blood vessel 7. This is particularly purposeful in the case of smaller blood vessels, namely those with an outer diameter of less than 8 mm. In the case of blood vessels with larger cross-sections, the longitudinal extension of the irradiating and receiving surface can be somewhat smaller.

In the case of large blood vessels, for example with an outer diameter of more than 15 mm such as the aorta, an ultrasonic probe with a probe head of the kind shown as an example in FIGS. 4 to 6 is recommended. In this exemplified embodiment, the probe head 8 attached to the probe cable 1 is also rod-shaped and can also consist of stainless steel as in the case of the exemplified embodiment according to FIGS. 1 to 3. Also in this exemplified embodiment, a piezoelectric crystal is provided in the probe head in the vicinity of the forward end face 9 of the probe head and has a planar or slightly curved irradiating and receiving surface 10 which is set back with respect to the circular peripheral cross section of the head, but usefully can have a larger longitudinal extension then the irradiating and receiving surface 4 of the first exemplified embodiment.

The holding wires 11 secured at the rearward end of the probe head 8 to two opposing sides of the head have a different shape then the fastening wires 5 in the embodiment according to FIGS. 1 to 3. While they can also usefully consist of stainless spring steel as in the afore-mentioned embodiment and extend from their rearward end initially beside the probe head parallel to its longitudinal extension, they spread apart linearly at an angle to the probe head in the region of the elongate irradiating and receiving surface 10, and as in the case of the fastening wires of the afore-mentioned embodiment, are provided at their ends with enlargements 12.

The holding wires formed and shaped in this manner do not serve as a clasp by means of which the probe head is placed onto the blood vessel as in the case of the wires in the previously described exemplified embodiment, rather they are designed to clamp the probe head between the blood vessel 13 and adjacent supporting tissue 14 of the patient and hold it in this position. This takes place on account of their alignment and position in such a manner that the irradiating and receiving surface 10 of the piezoelectric crystal in the position fastened to the blood vessel 13 by means of the holding wires 11 extends with its longitudinal extension substantially perpendicularly to the blood flow direction and with its transverse extension at an angle of approximately 45° to the blood flow direction.

Figure 7:
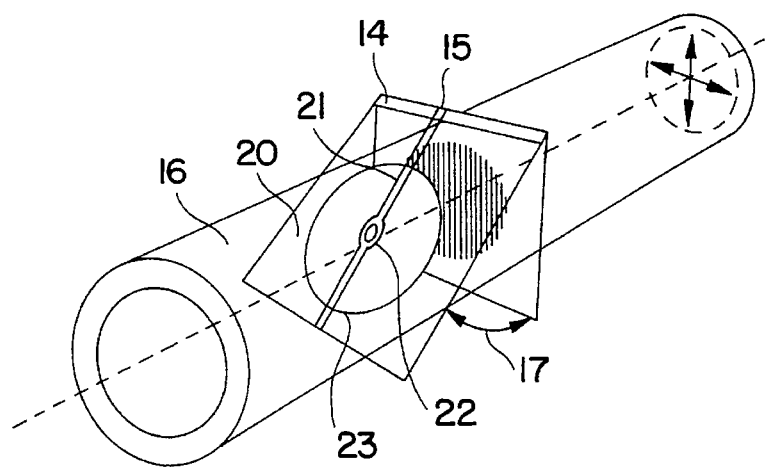
FIGS. 7, 8 and 9 show the positioning, irradiating and receiving surface of the sensor with respect to a blood vessel within various unavoidable tolerances.
Figure 8:
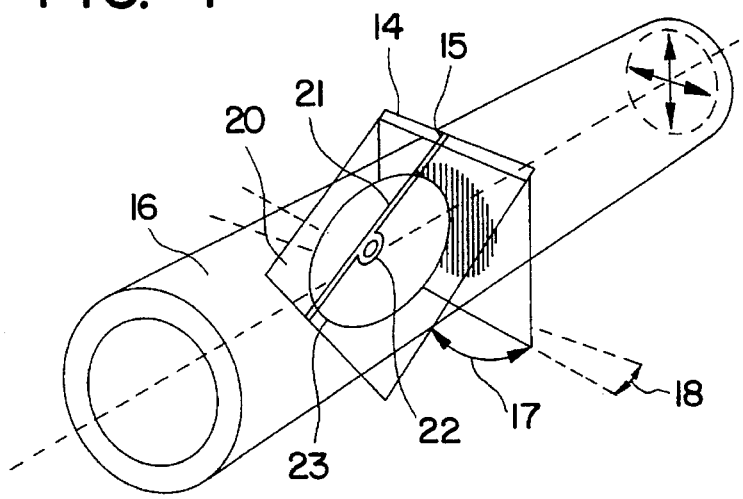
Figure 9:
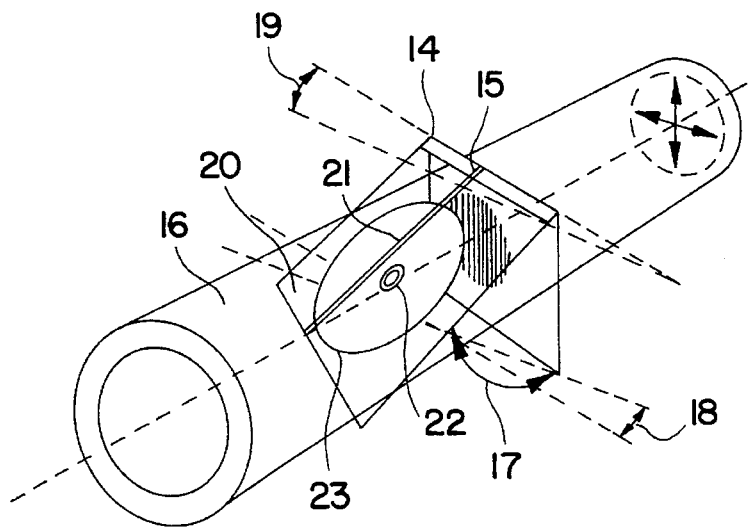

FIGS. 7 to 9 show the effect of the inventive measuring probe and of a conventional ultrasonic probe with a relatively small quadratic or circular irradiating and receiving surface 14 in different exact alignments of the measuring probe with respect to the blood vessel 16. The figures show that the orientation of the irradiating and receiving surfaces 14, 15 can in both cases lie within an unavoidable tolerance range within 3 dimensions.

FIG. 7 shows the orientation of the irradiating and receiving surface in the ideal position without any tolerance deviation from the target position.

The inclination of the irradiating surface with respect to the blood vessel direction (angle 17) is ideally 45° to 65° in the example shown. A deviation of the longitudinal extension of the irradiating surface to the perpendicular on the blood flow direction is 0° in both dimensions in FIG. 7. FIG. 7 shows that in the case of these exactly maintained angles (tolerance 0°), no difference exists in the measuring accuracy between the inventive irradiating surface 14 and the conventional irradiating surface 15. The ultrasonic fan 20 emitting from the inventive irradiating surface 14 and the ultrasonic beam 21 from the conventional irradiating surface 15 both detect the fastest blood flow velocities in the centre 22 of the blood vessel 16 as well as the slowest blood flow velocities at the inner wall 23 of the vessel.

FIG. 8 shows the situation in which a small deviation of the alignment of the irradiating surfaces 14, 15 occurs in the second dimension (tolerance angle 18). Here, the ultrasonic fan 20 of the inventive irradiating surface 14 cuts the center 22 of the blood vessel 16 as in the case of FIG. 7 and thus registers the fastest blood flow velocities as in the case of FIG. 7. In contrast, the ultrasonic beam 21 of the conventional ultrasonic probe intersects to the side of the center of the blood vessel so that the fastest blood flow velocities at that location are no longer detected by the probe. In contrast, the slowest blood flow velocities at the inner wall of the vessel are detected by both irradiating surfaces.

FIG. 9 shows the situation in the case of an additional tolerance deviation in the third dimension (angle 19). The ultrasonic beam 21 of the conventional irradiating surface 15 is pivoted more strongly away from the center 22 of the blood vessel in comparison to the situation in FIG. 8. As blood vessels ideally have a parabolic flow profile, a considerable measurement error will occur in the case of FIG. 9 because the maximum flow velocities in the center of the blood vessel are not detected. In contrast, in the case of the ultrasonic fan 20 of the inventive irradiating surface 14, both the central maximum velocities as well as the slower velocities at the vessel inner wall 23 are completely detected.

I claim:

1. An implantable measuring probe for measuring the flow velocity of blood in a natural blood vessel or a replacement blood vessel of humans and animals, comprising:

a rod-shaped probe head arranged at an end of a probe cable;

a sensor inserted in said probe head; and a device attached to said probe head to hold said probe head on the blood vessel, said sensor including an irradiating and receiving surface having an elongate form and a longitudinal extension being at least as large as an inner diameter of the blood vessel in which the measurement is to be carried out, said surface extending with said longitudinal extension substantially parallel to a longitudinal axis of the rod-shaped probe head and oriented with respect to the holding device to extend with said longitudinal extension approximately perpendicularly to the blood flow direction in said blood vessel with said probe head being secured to the blood vessel via said device.

2. A probe according to claim 1, wherein said longitudinal extension of the irradiating and receiving surface is at least 1½ times the inner diameter of the blood vessel.

3. A probe according to claim 1, wherein a length of the irradiating and receiving surface is at least 1½ times a width of the irradiating and receiving surface.

4. A probe according to claim 1, wherein said longitudinal extension of the irradiating and receiving surface is at least 2½ times a width of the irradiating and receiving surface.

5. A probe according to claim 1, wherein said irradiating and receiving surface has a transverse extension and is oriented with respect to the holding device to extend with said transverse extension at an angle of 0° to 90° to the blood flow direction with the probe head being secured to the blood vessel.

6. A probe according to claim 1, wherein said irradiating and receiving surface has a transverse extension and is orientated to the holding device to extend with said transverse extension at an angle of approximately 30° to 60°, depending on a size of the blood vessel, when the probe head is secured to the blood vessel.

7. A probe according to claim 1, wherein said irradiating and receiving surface of the probe is formed by a plurality of sensors.

8. A probe according to claim 1, wherein said irradiating and receiving surface of the sensor is arranged directly in front of a forward end of the rod-shaped probe head distant from the probe cable on a longitudinal side of the probe head.

9. A probe according to claim 1, wherein said irradiating and receiving surface of the sensor extends substantially across an entire cross-sectional width of the rod-shaped probe head.

10. A probe according to claim 1, wherein said holding device includes at least one clasp mounted on the probe head and securable with the probe head to the blood vessel.

11. A probe according to claim 10, wherein said at least one clasp is formed by the probe head and at least one band or wire piece which is secured with its one end approximately at or near a rear end of the rod-shaped probe head connected to the probe cable and extends at one side of the probe head substantially in a longitudinal direction.

12. A probe according to claim 11, wherein said at least one band or wire piece ends with its other free end near or directly near a forward end of the probe head distant from the probe cable.

13. A probe according to claim 11, wherein said at least one band or wire piece projects with its other free end beyond a forward end of the probe head distant from the probe cable.

14. A probe according to claim 11, wherein said band or wire piece is bent away from the probe head with a bulge-shaped form in a region of the irradiating and receiving surface.

15. A probe according to claim 11, wherein said band or wire piece is flexibly elastic in such a manner that the probe head placed on the blood vessel can be pulled off the blood vessel by pulling at the probe cable in the longitudinal direction of the probe head.

16. A probe according to claim 10, wherein said clasp has at least two fastening wires including wire pieces which are secured respectively to one side of the probe head.

17. A probe according to claim 16, wherein said two fastening wires are bent away in a bulge-like form from the probe head in a region of the irradiating and receiving surface of the sensor.

18. A probe according to claim 17, wherein a spacing between the two fastening wires in a longitudinal area of said bulge-like form is substantially greater than at both ends of said two fastening wires.

19. A probe according to claim 10, wherein said holding device has at least two holding wires each secured respectively to one side of the probe head and which substantially linearly spread apart from one another and the probe head in a direction of a forward end of said two holding wires.

20. A probe according to claim 11, wherein free ends of the band or wire piece are rounded off.

21. A probe according to claim 11, wherein free ends of the band or wire piece are provided with round enlargements.

22. A method of measuring a flow velocity in a blood vessel which is either a natural blood vessel or a replacement blood vessel of humans and animals, comprising the steps of:

using an implantable measuring probe or ultrasonic probe having a probe head which is arranged at the end of a probe cable;

determining a blood flow direction in the blood vessel and a size of the blood vessel; and arranging an elongate irradiating and receiving surface of the probe head on the blood vessel such that a longitudinal extension of the irradiating and receiving surface extends approximately perpendicularly to the blood flow direction in the blood vessel and a transverse extension of the irradiating and receiving surface extends at an angle of 0° to 90° to the blood flow direction depending on the size of the blood vessel.

23. A probe according to claim 1, wherein said implantable measuring probe is an ultrasonic probe.

24. A probe according to claim 1, wherein said sensor is a piezoelectric crystal.

25. A probe according to claim 1, wherein said longitudinal extension of said irradiating and receiving surface is 3½ times the width of said surface.

* * * * *